(12) United States Patent
Leeuwen et al.

(10) Patent No.: US 8,779,164 B2
(45) Date of Patent: Jul. 15, 2014

(54) PHOSPHINE-BASED CATALYSTS USEFUL FOR THE TELOMERIZATION OF BUTADIENE

(75) Inventors: Petrus Van Leeuwen, Kockengen (NL); Mathieu Tschan, Tarragona (ES); Zoraida Freixa, Tarragona (ES); Henk Hagen, Terneuzen (NL)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 13/518,040

(22) PCT Filed: Feb. 17, 2010

(86) PCT No.: PCT/ES2010/070086
§ 371 (c)(1),
(2), (4) Date: Jun. 21, 2012

(87) PCT Pub. No.: WO2011/101504
PCT Pub. Date: Aug. 25, 2011

(65) Prior Publication Data
US 2013/0123516 A1    May 16, 2013

(51) Int. Cl.
*C07F 19/00* (2006.01)
*C07C 1/22* (2006.01)

(52) U.S. Cl.
USPC .......................................... 549/212; 585/251

(58) Field of Classification Search
USPC .......................................... 549/212; 585/251
See application file for complete search history.

(56) References Cited

U.S. PATENT DOCUMENTS

| | | | |
|---|---|---|---|
| 7,026,523 B2 | 4/2006 | Rottger et al. | |
| 7,030,286 B2 | 4/2006 | Rottger et al. | |
| 7,141,539 B2 | 11/2006 | Edwards | |
| 7,425,658 B2 | 9/2008 | Edwards | |
| 2004/0059170 A1 | 3/2004 | Rottger et al. | |
| 2005/0038305 A1 | 2/2005 | Edwards | |
| 2008/0000812 A1 | 1/2008 | Reistad et al. | |
| 2011/0137086 A1 | 6/2011 | Briggs et al. | |

FOREIGN PATENT DOCUMENTS

| | | |
|---|---|---|
| EP | 561779 A1 | 9/1993 |
| EP | 461222 B2 | 4/2001 |
| WO | 92/10450 A1 | 6/1992 |
| WO | WO 9210450 A1 * | 6/1992 |
| WO | 03/031379 A1 | 4/2003 |
| WO | 2004/002931 A1 | 1/2004 |
| WO | 2006024614 A1 | 3/2006 |
| WO | 2006024615 A1 | 3/2006 |
| WO | 2006024616 A1 | 3/2006 |
| WO | 2007085321 A1 | 8/2007 |

OTHER PUBLICATIONS van Leeuwen, P. W. N. M., Alcoholysis of Acylpalladium(II) Complexes Relevant to the Alternating Copolymerization of Ethene and Carbon Monoxide and the Alkoxycarbonylation of Alkenes: the Importance of Cis-Coordinating Phosphines, 2003, J. Am. Chem. Soc., 125, 5523-5539).*
Jackstell, R., An Industrially Viable Catalyst System for Palladium-Catalyzed Telomerizations of 1,3-Butadiene with Alcohols, 2004, Chem. Eur. J., 10, 3891-3900.*
Angewandte Chemie, Int. Ed. 2002, 41, 6, 986.
Angewandte Chemie, Int. Ed. vol. 42 No. 11 2003 1284-1287.
Chem. Eur. J. 2004, 10, 16, 3891.
J. Mol. Catal. A, Chem. 2002, 185, 105.
PCT/ES2010/070086, International Search Report and Written Opinion, (2010).
PCT/ES2010/070086, International Preliminary Report on Patentability, (2010).

* cited by examiner

*Primary Examiner* — Kortney L. Klinkel
*Assistant Examiner* — John Mauro

(57) ABSTRACT

A phosphine-based catalyst composition suitable for the telomerization of butadiene to produce 1-octene includes palladium and one of a class of novel phosphine ligands characterized by two potentially functionalized phenyl rings and cyclized 5- or 6-member alkoxy groups that, together, bridge the two potentially functionalized phenyl rings. In these groups the alkoxy moiety of each is located ortho to at least one functionalizing moiety, if any, on the phenyl rings. The catalysts including this class of phosphine ligands may exhibit higher catalytic activity and selectivity, and may be used at lower temperatures, than many other phosphine ligand catalysts, reducing costs. Palladium precipitation may also be reduced.

1 Claim, No Drawings

PHOSPHINE-BASED CATALYSTS USEFUL FOR THE TELOMERIZATION OF BUTADIENE

BACKGROUND

1. Field of the Invention

The invention relates to the field of phosphine-based catalysts. More particularly, it relates to new phosphine-based ligands that are useful in preparing catalysts that show improved performance in the telomerization of butadiene.

2. Background of the Art

It is generally known that 1-octene may be efficiently prepared via the telomerization of butadiene. This telomerization is typically done in the presence of methanol, and the catalyst is frequently a combination of a Group VIII metal, such as palladium, and a known phosphine ligand. The telomerization is frequently a three-step process. In the first step, butadiene is telomerized together with methanol to yield 1-methoxy-2,7-octadiene ("MOD-1"). In the second step, MOD-1 is hydrogenated to yield methyloctylether. In step three, the methyloctylether undergoes ether cleavage to yield 1-octene and methanol.

One known method of accomplishing the telomerization step uses a catalyst that is a combination of a palladium salt and triphenylphosphine (TPP). However, less than desirable yields of 1-octene are encountered when using this phosphine. This appears to be due, at least in part, to side reactions that lead to formation of 3-methoxy-1,7-octadiene ("MOD-3") and 1,3,7-octatriene.

Another approach is disclosed in U.S. Pat. No. 7,425,658, which teaches a method for producing 1-octene from butadiene by dimerizing and alkoxylating butadiene in the presence of one or more alkoxy-substituted phosphine ligands. This is done under alkoxydimerization conditions with an alkoxydimerization catalyst. Illustrative phosphine ligands include tris(2,4,6-trimethoxyphenyl)phosphine and tris-(4-methoxyphenyl)phosphine.

Co-pending International Application No. PCT/US09/051,347, filed on Jul. 22, 2009, teaches telomerization of 1,3-butadiene in the presence of an organic hydroxyl compound, a palladium (Pd) catalyst and at least one of a group of novel phosphine ligands. Illustrative phosphine ligands include tris-(2-methoxyphenyl) phosphine, tris-(2,4-dimethoxy-phenyl) phosphine, bis-(2-methoxyphenyl)phenylphosphine, tris-(2-methoxy-4-fluorophenyl)-phosphine and tris-(2-methoxy-4-chlorophenyl)phosphine.

U.S. Pat. No. 7,026,523 discloses a method for telomerizing non-cyclic olefins that includes use of a Pd-carbene complex as a catalyst.

Unfortunately, none of the known methods appears to satisfactorily achieve the goals of increased levels of catalytic activity and yield, combined with reductions of undesired side products. Because of this, producers of 1-octene via the butadiene telomerization route continue to search for new catalysts that offer improvements in any or all of these goals. The present invention addresses this need.

SUMMARY OF THE INVENTION

In one embodiment, this invention provides a catalyst composition suitable for use in the telomerization of butadiene to MOD-1. The composition comprises palladium and a phosphine ligand represented by any of the following formulas:

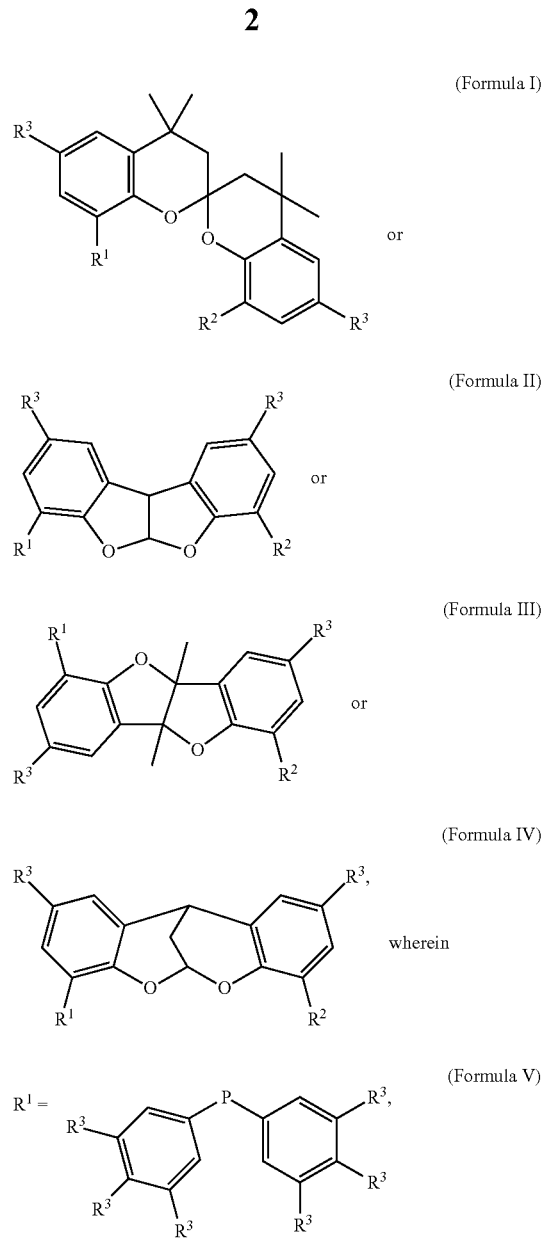

$R^2$ is H or $R^1$, and each $R^3$ is independently selected from H; linear, branched or cyclic $C_1$-$C_{20}$ alkyl, $C_6$-$C_{18}$ aryl, and $C_1$-$C_{20}$ alkoxy; $C_1$-$C_{20}$ dialkylamino; halogen; and trifluoromethyl.

In another embodiment, the invention provides a process to prepare a catalyst composition, comprising contacting palladium and a phosphine ligand corresponding to any of Formulas I, II, III or IV, under conditions such that a catalyst composition is formed.

In yet another embodiment, the invention provides a process to prepare 1-octene comprising the steps of (i) reacting 1,3-butadiene with a primary aliphatic alcohol or an aromatic hydroxyl compound having the formula R—H (Formula VI)

in the presence of the catalyst composition comprising palladium and a phosphine ligand corresponding to any of Formulas I, II, III or IV, to form a 1-substituted-2,7-octadiene of the formula $CH_2$=CH—$CH_2$—$CH_2$—$CH_2$—CH=CH—$CH_2$—R (Formula VII)

wherein R represents a residue of the primary aliphatic alcohol or the aromatic hydroxyl compound; (ii) subjecting the 1-substituted-2,7-octadiene formed in step (a) to hydrogenation in the presence of a hydrogenation catalyst to form a 1-substituted octane of the formula $$CH_3-CH_2-CH_2-CH_2-CH_2-CH_2-CH_2-CH_2-R;$$ (Formula VIII)

and (iii) decomposing the 1-substituted octane formed in step (b) in the presence of a suitable catalyst to form 1-octene.

DETAILED DESCRIPTION OF THE EMBODIMENTS

The novel phosphine ligands of the invention have been found, in many embodiments and particularly in catalyst complexes with Pd, to exhibit increased stability and a higher catalytic activity and/or selectivity, when compared with other known catalysts containing Pd and a phosphine ligand, in the production of 1-octene via the butadiene telomerization route. This higher activity enables the catalyst to be employed in, for example, an isothermal reactor system, at a lower temperature. When applied in an adiabatic reactor system, a lower inlet temperature can be used. In either case, and under similar feed conditions, the result is a lower average reactor temperature. This lower temperature, in turn, increases overall selectivity, which decreases formation of side products such as MOD-3 and 1,3,7-octatriene. Pd precipitation is also decreased. The end result is that production rates may be increased and energy costs reduced.

The inventive phosphine ligands have in common, in addition to two potentially functionalized phenyl rings, two cyclized 5- or 6-member alkoxy groups that, together, bridge the two potentially functionalized phenyl rings. In these groups the alkoxy moiety of each is located ortho to at least one functionalizing moiety, if any, on the phenyl rings. In these embodiments the phosphine ligand is represented by any of Formulas I, II, III, and IV, including $R^1$ as defined in Formula V.

Ligand synthesis may be carried out via a multi-step process. In step one, the organic backbone, for example, 4,4,4',4',6,6'-hexamethylspiro-2,2'-bichroman, is brominated at the position ortho to the oxygen atom When desired, the bromination conditions can be adjusted to achieve bromination of both phenyl rings by adjusting the stoichiometry of the reaction. In step two, the monobrominated or dibrominated organic fragment is lithiated. In step three, electrophilic substitution of the monolithiated or dilithiated species is effected, using a phosphine, preferably chlorodiphenylphosphine (ClPPh$_2$). In step four, the phosphine ligand is recovered by, for example, filtration and solvent removal.

Exemplary ligands of the invention conforming to Formulas I through IV include, in non-limiting embodiments, (4,4,4',4',6,6'-hexamethyl-2,2'-spirobis[chroman]-8-yl)diphenylphosphine (Formula IX); (2,9-dimethyl-5a,10b-dihydrobenzo[b]benzofuro[3,2-d]furan-4-yl)diphenylphosphine (Formula X); (2,9-dimethyl-5a,10b-dihydrobenzo[b]benzofuro[3,2-d]-furan-4,7-diyl)bis(diphenylphosphine) (Formula XI); (3,4b,8,9b-tetramethyl-4-b,9b-dihydro-benzo[b]benzofuro[2,3-d]-furan-1,6-diyl)bis(diphenylphosphine) (Formula XII), 2,10-di-t-butyl-4-diphenylphosphino-6,12-methano-12H-dibenzo[2,1-d:1',2"-g][1,3]dioxocin (Formula XIII), 2,10-dimethyl-4-diphenylphosphino-6,12-methano-12H-dibenzo[2,1-d:1',2"-g][1,3] dioxocin (Formula XIV), and 2,10-dimethyl-4,8-diphenylphosphino-6,12-methano-12H-dibenzo-[2,1-d:1',2"-g][1,3]dioxocin (Formula XV). These ligands may be used alone or in combinations of two or more in a single catalyst package. These exemplary ligands may be illustrated by means of the following structures:

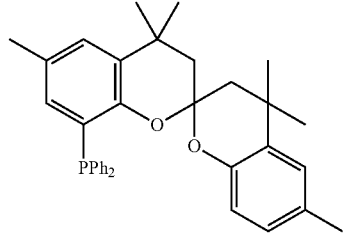

(Formula IX)

(4,4,4',4',6,6'-hexamethyl-2,2'-spirobi[chroman]-8-yl)diphenylphosphine

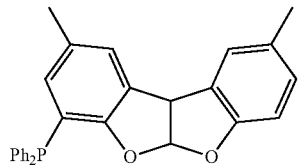

(Formula X)

(2,9-dimethyl-5a,10b-dihydrobenzo[b]benzofuro[3,2-d]furan-4-yl)diphenylphosphine

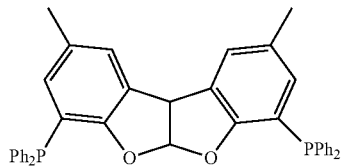

(Formula XI)

(2,9-dimethyl-5a,10b-dihydrobenzo[b]benzofuro[3,2-d]furan-4,7-diyl)bis(diphenylphosphine)

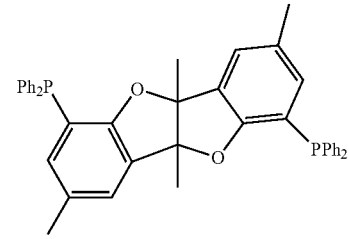

(Formula XII)

(3,4b,8,9b-tetramethyl-4b,9b-dihydrobenzo[b]benzofuro[2,3-d]furan-1,6-diyl)bis(diphenylphosphine)

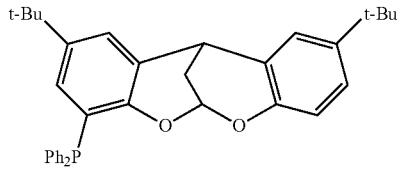

(Formula XIII)

2,10-di-t-butyl-4-diphenylphosphino-6,12-methano-12H-dibenzo[2,1-d:1',2"-g][1,3]dioxocin -continued

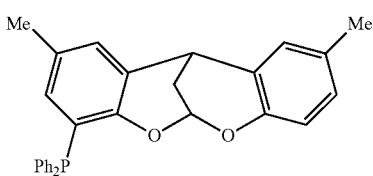

(Formula XIV)

2,10-dimethyl-4-diphenylphosphino-6,12-
methano-12H-dibenzo[2,1-d:1',2"-g][1,3]
dioxocin

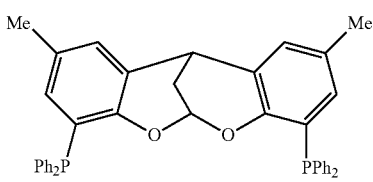

(Formula XV)

2,10-dimethyl-4,8-diphenylphosphino-6,12-
methano-12H-dibenzo[2,1-d:1',2"-g][1,3]
dioxocin Processes for producing 1-octene from a telomerization product mixture comprising the starting 1-substituted-2,7-octadiene are known and extensively described in literature. See, for example, United States Application Publication 2005/0038305 and U.S. Pat. No. 7,030,286. In general, a three-step process may be suitably employed. In this process, the first step preferably occurs in a reaction fluid that comprises the 1,3-butadiene, a primary aliphatic alcohol or aromatic hydroxyl compound, and the telomerization catalyst, which is a complex of Pd and one or more of the inventive phosphine-based ligands. The phosphine ligand is preferably present in an amount sufficient to stabilize the Pd. The amount of each advantageously provides an initial phosphine ligand-to-Pd ratio of from 1.0, preferably from at least 1.5, to 50, and preferably to 40. The reaction fluid may further comprise one or more optional component(s), such as an organic solvent, a catalyst promoter, a catalyst stabilizer, or a butadiene polymerization inhibitor.

This first step advantageously occurs under an inert atmosphere, such as nitrogen, argon, or helium, and at a reaction temperature sufficient to produce the 1-substituted-2,7-octadiene. The substituent is the residue of the primary aliphatic alcohol or aromatic hydroxyl compound. The reaction temperature is preferably greater than 40 degrees Celsius (° C.), more preferably greater than (>) 50° C., and still more preferably >60° C., and is preferably less than (<) 120° C., more preferably <110° C., and still more preferably <100-C. The product of the first step is the telomerized product, which is the 1-substituted-2,7-octadiene, for example, 1-methoxy-2,7-octadiene (MOD-1).

In the second step, the 1-substituted-2,7-octadiene, for example, MOD-1, is hydrogenated to yield the substituted octylether, for example, methyloctylether. In, general any conventional hydrogenation process can be used. The hydrogenation may be carried out in the liquid phase, or in the vapor phase. Depending on the nature of the starting material, the reaction can be carried out at a temperature from 0° C. to 400° C. Preferably, the temperature ranges from ambient to 350° C. More preferably the hydrogenation is carried out at a temperature from 50° C. to 200° C. The pressure is not critical and depends on whether the hydrogenation is carried out in the liquid or in the vapor phase. In general the pressure can vary from 0.1 to 100 bar (10 kilopascals (kPa) to 10,000 kPa).

Finally, in step three, the octylether, for example, methyloctylether, undergoes ether cleavage to yield 1-octene and an alcohol, for example, methanol. In this step any conventional catalyst which is capable of decomposing the methyloctylether to form 1-octene may be used. A solid acid catalyst, preferably an alumina catalyst, may be used for this purpose. Examples of such catalysts may include alpha, delta, gamma, eta and theta aluminas, which may be modified by bases such as sodium hydroxide, or by other treating agents. In certain particular embodiments gamma alumina is employed.

The temperature at which the decomposition is carried out depend on both the catalyst activity and the decomposition temperature of the respective compound being decomposed. In particular embodiments, for example, where the compound being decomposed is methyloctylether, the decomposition temperature may range up to 500° C., preferably from 200° C. to 400° C., and more preferably from 250° C. to 350° C. The pressure under which the decomposition reaction may be carried out can also vary widely, but is preferably maintained from 1 to 2 bar (100 kPa to 200 kPa) in order to ensure high activity.

The third step can be carried out in the vapor or the liquid phase, the vapor phase being frequently preferred. An inert gas or an inert liquid diluent may be used to dilute the reactant, for example, methyloctylether. Examples of such inert gases may include nitrogen, helium, argon, and combinations thereof. Alternatively, another ether may be used as a diluent. When employed, the diluent is desirably in a weight ratio, diluent-to-reactant, ranging from >0:1 to 100:1, and preferably from 1:1 to 20:1. Selection of an ether as a diluent may offer some advantage by enabling recycle, which may in turn help to reduce net alcohol loss. For instance, where methyloctylether is selected as a diluent, some methanol will be produced in the decomposition reaction. This methanol then dehydrates to form dimethylether (DME) and water, and this reaction occurs simultaneously with the ether cleavage reaction to yield 1-octene and methanol. If the produced DME is then recycled back to the decomposition reactor, water may then also be added, which will help to ensure that there is no net alcohol loss across the process. The produced methanol can also be recycled, back to the first process step.

The overall reaction may be carried out continuously, semi-continuously or batchwise. In the continuous mode the reactant(s) and, where used, any diluent(s) may be passed continuously over a catalyst bed under the desired reaction conditions. The reactant(s) may be added to the reactor at a weight hour space velocity (WHSV) ranging from 0.01 gram of 1-substituted octane per gram catalyst per hour (g 1-substituted octane/g catalyst/h) to 50 g of 1-substituted octane/g catalyst/h, preferably from 0.1 g of 1-substituted octane/g catalyst/h to 10 g of 1-substituted octane/g catalyst/h.

The overall reaction may be carried out isothermally or, alternatively, adiabatically. In case of fixed bed adiabatic operation, the temperature in the reactor will generally drop over the reactor's length, due to the endothermic nature of the reaction. The exit temperature of the reactor should desirably remain above the dew point of the effluent mixture, in order to reduce or avoid condensation of liquids onto the catalyst. The initial inlet temperature and the extent of the temperature drop correlate to the level of conversion of the 1-substituted octane to 1-octene and also to the ratio of diluent to reactant, i.e., a greater temperature drop indicates a higher conversion level, and a higher diluent-to-reactant ratio tends to lead to a higher conversion level at a given inlet temperature. In preferred embodiments the molar conversion of 1-substituted octane to 1-octene, using the novel phosphine-based catalysts of the invention, may range from 40 to 80 percent of theoretical, based on the inlet concentration of the 1-substituted octane.

The following examples are provided for illustrative purposes only. Those skilled in the art will be able to discern modifications and alterations that may be employed without departing from the spirit of the invention.

EXAMPLES

Example 1

(a) Synthesis of 4-bromo-4,4,4',4',6,6'-hexamethyl-spiro-2,2'-bichroman

An amount of a starting material ("backbone") 4,4,4',4',6,6'-hexamethylspiro-2,2'-bichroman (2 grams (g), 5.9 micromoles (mmol)) and N-bromosuccinimide (NBS) (1.05 g, 5.9 mmol) are dissolved in dimethylformamide (DMF) (100 milliliters (mL)) and stirred at room temperature for one day. The conversion of the starting 4,4,4',4',6,6'-hexamethylspiro-2,2'-bichroman is monitored by gas chromatography/mass spectroscopy (GC/MS). The solvent is evaporated to dryness and the solid is washed with water and extracted with ether. The ether is dried over magnesium sulfate ($MgSO_4$) and evaporated to dryness. The obtained solid is washed with ethanol to give 2 g of a white solid that contains a mixture of monobrominated, dibrominated, and unconverted 4,4,4',4',6,6'-hexamethylspiro-2,2'-bichroman in a 65/15/20 ratio. This product mixture is used in step (b) without further purification.

(b) Synthesis of (4,4,4',4',6,6'-hexamethyl-2,2'-spirobis[chroman]-8-yl)diphenylphosphine (Formula IX)

A solution of the unpurified 8-bromo-4,4,4',4',6,6'-hexamethylspiro-2,2'-bichroman from step (a) (2.2 g, containing 65 percent 8-bromo-4,4,4',4',6,6'-hexamethylspiro-2,2'-bichroman, 3.44 mmol) in tetrahydrofuran (THF) (40 milliliters (mL)) is cooled down to −78° C. Then, n-butyllithium (n-BuLi) (2.5 molar (M) in hexane, 1.9 mL) is added slowly. To this reaction mixture is added $ClPPh_2$ (1 equivalent (eq), 0.46 mL) at −78-C. The mixture is stirred at −78° C. for 1 hour (hr) and at room temperature (RT) for 1 hr. Then the solvent is evaporated and degassed water is added. The product is extracted with dichloromethane. The organic layer is separated and dried over magnesium sulfate ($MgSO_4$). Evaporation of the solvent gives 2.2 g of crude product, which is then purified by means of a chromatography column on silica gel. The product is isolated as a white solid (1 g, 1.92 mmol, yield 55 percent (%) of theoretical) and comprises (4,4,4',4',6,6'-hexamethyl-2,2'-spirobis[chroman]-8-yl)diphenyl-phosphine.

Example 2

(a) Synthesis of 4-bromo-2,8-dimethyl-5a,10b-dihydrobenzofuro[2,3-b]benzofuran

The backbone 2,8-dimethyl-5a,10b-dihydrobenzofuro-[2,3-b]benzofuran (1.5 g, 6.3 mmol) and NBS (2.016 g, 11.3 mmol) are dissolved in DMF (100 mL) and stirred at RT for 1 day (flask is covered with aluminium foil). The conversion is monitored by GC/MS. After three days, a mixture of the monobrominated product, the dibrominated product, and the unmodified backbone (monobromo/dibromo/backbone) is formed, in a 75/23/2 ratio, based on weight percents. The solvent is evaporated to dryness and the solid is washed with water and extracted with dichloromethane. The dichloromethane solution is then dried over $MgSO_4$ and evaporated to dryness. The solid obtained is washed with ethanol to give a white solid (1.5 g, containing a mixture of monobromo/dibromo, 75/25). This product ("bromobackbone") is used in step (b) without further purification.

(b) Synthesis of 4-diphenylphosphine-2,8-dimethyl-5a,10b-dihydrobenzofuro[2,3-b]benzofuran (Formula X)

A solution of the step (a) unpurified bromobackbone (1.5 g, containing 3.55 mmol of 4-bromo-2,8-dimethyl-5a,10b-dihydrobenzofuro[2,3-b]benzofuran) in THF (40 mL) is cooled down to −78° C. Then, n-BuLi (2.5 molar (M) in hexane, 2.8 mL) is added slowly. The mixture is stirred at −78° C. for 2 h and $ClPPh_2$ (1.065 mL) is added. The mixture is stirred at −78° C. for 2 h and at RT overnight. Then the solvent is evaporated and degassed water is added. The product is extracted with dichloromethane. The organic layer is separated and dried over $MgSO_4$. Evaporation of the solvent gives a crude product which is purified by chromatography column on silica gel. The product is isolated, impure, as a white solid, then purified by preparative thin layer chromatography on silica and recovered as a white solid (0.23 g, 0.544 mmol, yield 15% of theoretical) comprising 4-diphenylphosphine-2,8-dimethyl-5a,10b-dihydrobenzofuro[2,3-b]benzofuran.

Example 3

(a) Synthesis of 4-bromo-2,8-dimethyl-5,10-methano-10H-dibenzo[2,1-d:1',2'-g][1,3]-dioxocin The backbone 2,8-dimethyl-5,10-methano-10H-dibenzo[2,1-d:1',2'-g][1,3]dioxocin (1.5 g, 5.95 mmol) and NBS (1.477 g, 8.29 mmol) are dissolved in DMF (100 mL) and stirred at RT for 1 day. The conversion is monitored by GC/MS. After three days, a mixture of the monobromo/dibromo/backbone is formed, in a 76/9/13 ratio. The solvent is evaporated to dryness and the solid is washed with water and extracted with dichloromethane. The dichloromethane solution is dried over $MgSO_4$ and evaporated to dryness. The solid obtained is washed with ethanol to give a white solid (1.5 g, containing a mixture of monobromo/dibromo 90/10), which is the bromobackbone. The solid bromobackbone is used in step (b) below without further purification.

(b) Synthesis of 4-diphenylphosphino-2,8-dimethyl-5,10-methano-10H-dibenzo[2,1-d:-1',2'-g][1,3]dioxocin (Formula XIV)

A solution of the unpurified bromobackbone from step (a) (1.5 g, containing 4.07 mmol of 4-bromo-2,8-dimethyl-5,10-methano-10H-dibenzo[2,1-d:1',2'-g][1,3]dioxocin) in THF (40 mL) is cooled down to −78° C. Then, n-BuLi (2.5 M in hexane, 2.4 mL) is added slowly. The mixture is stirred at −78° C. for 2 h and $ClPPh_2$ (1.0 mL) is added. The mixture is stirred at −78° C. for 2 h and at RT overnight. Then the solvent is evaporated and degassed water is added. The product is extracted with dichloromethane. The organic layer is separated and dried over $MgSO_4$. The product is purified by chromatography column on silica gel and obtained as a white solid (0.80 g, 1.83 mmol, yield 45% of theoretical), which comprises 4-diphenylphosphino-2,8-dimethyl-5,10-methano-10H-dibenzo[2,1-d:-1',2'-g][1,3]dioxocin.

Example 4

Telomerization performance testing is carried out in a 1 liter (L) Parr reactor made of electropolished stainless steel.

For each reaction, the Parr reactor's autoclave is filled with specified amounts of methanol, promoter (sodium methoxide, at a promoter-to-Pd molar ratio of 5 to 1) and inhibitor (diethyl hydroxylamine, approximately 20 parts per million parts by weight (ppm) based on total weight of methanol plus crude butadiene). The autoclave is closed, purged twice with low pressure nitrogen ($N_2$, 6 bar, 600 kilopascals (kPa)) to substantially remove any oxygen contained in the autoclave. It is then purged once with high pressure $N_2$ (20 bar, 2,000 kPa) to test for leaks.

Following the leak test, a stainless steel sample cylinder is filled with a crude butadiene stream that contains approximately 50 weight percent (wt %) of 1,3-butadiene, based upon total crude butadiene stream weight. The contents of the sample cylinder are then pressure added to the autoclave with low pressure $N_2$ (6 bar, 600 kPa). The temperature in the autoclave is then raised to a desired work temperature (60° C., 75° C., 90° C., or 100° C., as shown in Table 2 hereinbelow).

To prepare the inventive catalyst, a standard catalyst, Pd acetylacetonate ($Pd(acac)_2$), is combined with two molar equivalents of the product (4,4,4',4',6,6'-hexamethyl-2,2'-spirobis[chroman]-8-yl)diphenylphosphine) prepared in Example 1. (One molar equivalent of acetic acid may be added to increase storage stability.) The inventive catalyst is then made by dissolving all three components in methanol, such that the Pd concentration in the methanol equals about 500 ppm. [Table 1 shows the structure of the (4,4,4',4',6,6'-hexamethyl-2,2'-spirobis[chroman]-8-yl)diphenylphosphine used in this example and correlates ligand structure and formulation with this Example 4, succeeding Examples 5-10, and succeeding Comparative Example A.]

The catalyst solution is weighed into a dry box, in an amount such that the Pd concentration will equal 10 ppm, based upon total weight of the methanol and butadiene reactants. This solution is then put into a stainless steel sample cylinder, and then pressure-added to the autoclave using high pressure $N_2$ (19 bar to 20 bar, or 1900 kPa to 2000 kPa). Following catalyst addition, a reaction begins, producing a final product. Samples are taken from the autoclave at set times (five minutes after catalyst addition and at 30-minute intervals thereafter), and gas and liquid phases thereof are analyzed via gas chromatography (GC).

Pd precipitation in the reactor is determined by measuring the Pd concentration in the liquid phase after the reaction, then comparing that to a theoretical number based on total amount of Pd added and total liquid volume, including liquids added at the beginning of the reaction and liquids formed due to the butadiene conversion. The Pd concentration in the liquid is measured using Inductively Coupled Plasma Atomic Emission Spectroscopy (ICP-AES). Testing is then carried out for conversion, selectivity to MOD-1, and Pd precipitation, at methanol-to-butadiene ratios of 2, 2.6 and 5, weight/weight (w/w), and results are recorded in Table 2. Table 3 shows catalyst activity in terms of butadiene conversion over two time periods.

Example 5

Example 4 is replicated except two molar equivalents of (2,9-dimethyl-5a,10b-dihydrobenzo[b]benzofuro[3,2-d]furan-4-yl)diphenylphosphine (Formula X) are used instead of the (4,4,4',4',6,6'-hexamethyl-2,2'-spirobis[chroman]-8-yl) diphenylphosphine as the ligand. Testing is done for conversion, selectivity to MOD-1 and Pd precipitation at a methanol-to-butadiene ratio of 2.6:1 and a reaction temperature of 90° C., and results are recorded in Table 2. Table 3 shows catalyst activity in terms of butadiene conversion over two time periods.

Example 6

Example 4 is again replicated, except one or two molar equivalents of (2,9-dimethyl-5a,10b-dihydrobenzo[b]benzofuro[3,2-d]furan-4,7-diyl)bis(diphenylphosphine) (Formula XI) is/are used. Testing is done as in Example 5 and results and activity shown in Tables 2 and 3.

Example 7

Example 4 is again replicated, except one or two molar equivalents of (3,4b,8,9b-tetramethyl-4-b,9b-dihydrobenzo[b]benzofuro[2,3-d]furan-1,6-diyl)bis(diphenyl-phosphine) (Formula XII) is/are used. Testing is again done as in Example 5, and results and activity are recorded in Tables 2 and 3.

Example 8

Example 4 is again replicated, except two molar equivalents of 2,10-di-t-butyl-4-diphenylphosphino-6,12-methano-12H-dibenzo[2,1-d:1',2"-g][1,3]dioxocin (Formula XIII) are used. Testing is again done as in Example 5, and results and activity are recorded in Tables 2 and 3.

Example 9

Example 4 is again replicated, except two molar equivalents of 2,10-dimethyl-4-diphenylphosphino-6,12-methano-12H-dibenzo[2,1-d:1',2"-g][1,3]dioxocin (Formula XIV) are used. Testing is again done as in Example 5, and results and activity are recorded in Tables 2 and 3.

Example 10

Example 4 is again replicated, except one or two molar equivalents of 2,10-dimethyl-4,8-diphenylphosphino-6,12-methano-12H-dibenzo[2,1-d:1',2"-g][1,3]-dioxocin (Formula XV) is/are used. Testing is again done as in Example 5, and results and activity are recorded in Tables 2 and 3.

Comparative Example A

Example 4 is again replicated, except two molar equivalents of triphenylphosphine are used. Testing is done as in Example 5 and further including Pd precipitation testing at methanol-to-butadiene ratios of 2 and 5 and temperatures of 60° C., 75° C., 90° C. and 100° C., and results and activity are recorded in Tables 2 and 3.

TABLE 1

| Sample Designation | Ligand |
|---|---|
| Example 4 | (4,4,4',4',6,6'-hexamethyl-2,2'-spirobi[chroman]-8-yl)diphenylphosphine (Formula IX) |
| Example 5 | (2,9-dimethyl-5a,10b-dihydrobenzo[b]benzofuro[3,2-d]furan-4-yl)diphenylphosphine (Formula X) |
| Example 6 | (2,9-dimethyl-5a,10b-dihydrobenzo[b]benzofuro[3,2-d]furan-4,7-diyl)bis(diphenylphosphine) (Formula XI) |
| Example 7 | (3,4b,8,9b-tetramethyl-4b,9b-dihydrobenzo[b]benzofuro[2,3-d]furan-1,6-diyl)bis(diphenylphosphine) (Formula XII) |
| Example 8 | 2,10-di-t-butyl-4-diphenylphosphino-6,12-methano-12H-dibenzo[2,1-d:1',2"-g][1,3]dioxocin (Formula XIII) |
| Example 9 | 2,10-dimethyl-4-diphenylphosphino-6,12-methano-12H-dibenzo[2,1-d:1',2"-g][1,3]dioxocin (Formula XIV) |
| Example 10 | 2,10-dimethyl-4,8-diphenylphosphino-6,12-methano-12H-dibenzo[2,1-d:1',2"-g][1,3]dioxocin (Formula XV) |
| Comparative Example A | Triphenylphosphine |

TABLE 2

| Ligand | Temp. (° C.) | MeOH/ Butadiene (wt/wt) | Butadiene conversion (% yield) | MOD-1 selectivity (%) | Palladium precip. (%)$^c$ |
|---|---|---|---|---|---|
| Comparative Example A | 60 | 2 | 32 | 91 | <5 |
| | 60 | 2.6 | 29 | 92 | 8 |
| | 60 | 5 | 17 | 92 | <5 |
| | 75 | 2.6 | 62 | 88 | <5 |
| | 90 | 2 | 82 | 80 | 16 |
| | 90 | 2.6 | 85 | 83 | 17 |
| | 100 | 2 | 84 | 73 | 18 |
| Example 4 | 40 | 2.6 | 30 | 93 | 5 |
| | 50 | 2.6 | 37 | 94 | 8 |
| | 60 | 2 | 71 | 93 | <5 |
| | 60 | 2.6 | 71 | 94 | <5 |
| | 60 | 5 | 63 | 94 | 11 |
| | 75 | 2.6 | 82 | 91 | <5 |
| | 90 | 2 | 93 | 87 | 19 |
| | 90 | 2.6 | 94 | 88 | 8 |
| | 100 | 2 | 92 | 83 | 32 |
| Example 5 | 90 | 2.6 | 80 | 88 | 43 |
| Example 6 | 90 | 2.6 | 63$^a$ | 86$^a$ | <5 |
| | | | 74 | 87 | <5 |
| Example 7 | 90 | 2.6 | 91$^a$ | 88$^a$ | 18$^a$ |
| | | | 91 | 89 | 7 |

TABLE 2-continued

| Ligand | Temp. (° C.) | MeOH/ Butadiene (wt/wt) | Butadiene conversion (% yield) | MOD-1 selectivity (%) | Palladium precip. (%)[c] |
|---|---|---|---|---|---|
| Example 8 | 90 | 2.6 | 96 | 90 | 23 |
| Example 9 | 90 | 2.6 | 92 | 89 | 22 |
| Example 10 | 90 | 2.6 | 79[a] | 86[a] | 12[a] |
|  |  |  | —[b] | —[b] | —[b] |

[a] Ligand/Pd ratio = 1.
[b] Pd(acac)$_2$ + ligand does not dissolve in methanol
[c] Estimated error of 5% absolute.

TABLE 3

| Ligand | Ligand/Pd ratio (mole/mole) | Butadiene conversion after 30 minutes (% yield) | Butadiene conversion after 150 minutes (% yield) |
|---|---|---|---|
| Comparative Example A | 2 | 29 | 85 |
| Example 4 | 2 | 74 | 94 |
| Example 5 | 2 | 56 | 80 |
| Example 6 | 1 | 35 | 63 |
|  | 2 | 40 | 74 |
| Example 7 | 1 | 80 | 91 |
|  | 2 | 48 | 91 |
| Example 8 | 2 | 77 | 96 |
| Example 9 | 2 | 62 | 92 |
| Example 10 | 1 | 48 | 79 |
|  | 2 | —[a] | —[a] |

[a] Pd(acac)$_2$ + ligand does not dissolve in methanol.

What is claimed is:

1. A process to prepare 1-octene comprising the steps of
   (i) reacting 1,3-butadiene with a primary aliphatic alcohol or an aromatic hydroxyl compound having the formula

R—H to form a 1-substituted-2,7-octadiene of the formula

CH$_2$=CH—CH$_2$—CH$_2$—CH$_2$—CH=CH—CH$_2$—R, in which R represents a residue of the primary aliphatic alcohol or the aromatic hydroxyl compound, in the presence of a catalyst composition comprising palladium and a phosphine ligand represented by any of the following formulas:

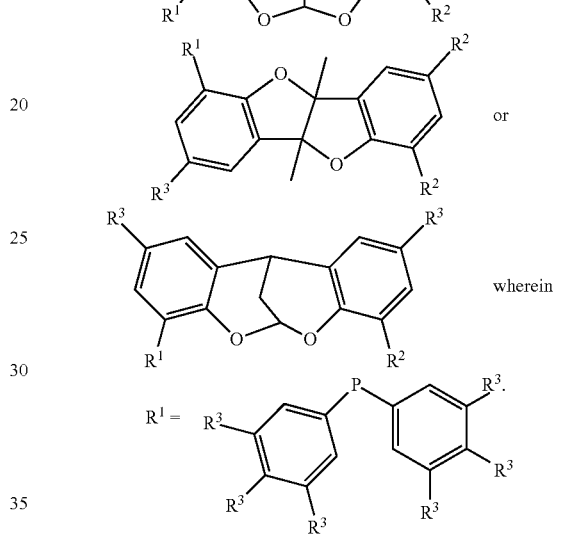

$R^2$ is H or $R^1$, and each $R^3$ is independently selected from H; linear, branched or cyclic $C_1$-$C_{20}$ alkyl, $C_6$-$C_{18}$ aryl, and $C_1$-$C_{20}$ alkoxy; $C_1$-$C_{20}$ dialkylamino; halogen; and trifluoromethyl; and (ii) subjecting the 1-substituted-2,7-octadiene formed in step (i) to hydrogenation in the presence of a hydrogenation catalyst, to form a 1-substituted octane of the formula CH$_3$—CH$_2$—CH$_2$—CH$_2$—CH$_2$—CH$_2$—CH$_2$—CH$_2$—R; and (iii) decomposing the 1-substituted octane formed in step (ii) in the presence of a suitable catalyst to form 1-octene.

* * * * *